United States Patent [19]

Spielvogel et al.

[11] Patent Number: 5,130,302
[45] Date of Patent: Jul. 14, 1992

[54] BORONATED NUCLEOSIDE, NUCLEOTIDE AND OLIGONUCLEOTIDE COMPOUNDS, COMPOSITIONS AND METHODS FOR USING SAME

[75] Inventors: Bernard F. Spielvogel, Raleigh; Anup Sood, Durham; Iris H. Hall, Chapel Hill; Barbara Ramsay Shaw, Durham, all of N.C.

[73] Assignee: Boron Bilogicals, Inc., Raleigh, N.C.

[21] Appl. No.: 453,311

[22] Filed: Dec. 20, 1989

[51] Int. Cl.$^5$ .................. A61K 31/00; C07H 19/00; C07H 21/00

[52] U.S. Cl. .......................... 514/45; 514/46; 514/47; 514/48; 514/49; 514/50; 514/51; 514/64; 536/23; 536/24; 536/27; 536/28; 536/29; 536/17.1

[58] Field of Search .............. 536/23, 27, 28, 29, 536/51, 4.1, 122, 18.1, 17.1; 514/45, 46, 49, 50, 51, 64; 424/1.1; 604/20

[56] References Cited

PUBLICATIONS

Schinazi et al., "Boron Compounds Suitable for Neutron Capture Therapy for ... Cancer", National Cancer Institute Workshop, May 3–4, 1988.
Cover Sheet for the North Carolina Biotechnology Center Competitive Grants Program. Project Entitled "Boron Nucleic Acids".
Cover Sheet for the North Carolina Biotechnology Center Economic Development Program. Project Entitled "Boronated Nucleosides".
"A Suitable Case for Irradiation", Borax Review, No. 3, 7 (1988).
Schinazi, R. et al., "Rational Design of Pyrimidines and Nucleosides for Neutron Capture Therapy," National Cancer Institute Workshop (May, 1988) (Pub. by National Cancer Institute), pp. 1–11.
Kabalka, G. et al., "Boron-11 MRI and MRS of Intact Animals Infused with a Boron Neutron Capture Agent," *Magnetic Resonance in Medicine* 8, 231 (1988).

*Primary Examiner*—Johnnie R. Brown
*Assistant Examiner*—J. Oliver Wilson
*Attorney, Agent, or Firm*—Bell, Seltzer, Park & Gibson

[57] ABSTRACT

A novel class of pharmaceutically active boronated nucleosides are provided. The nucleosides are boronated at a ring nitrogen of the purine or pyrimidine or analogues thereof. Also provided are phosphate esters of these nucleosides and oligomers thereof. Methods of making and using the boronated nucleosides are also disclosed.

14 Claims, No Drawings

BORONATED NUCLEOSIDE, NUCLEOTIDE AND OLIGONUCLEOTIDE COMPOUNDS, COMPOSITIONS AND METHODS FOR USING SAME

FIELD OF THE INVENTION

This invention pertains to novel Boron containing compounds having pharmaceutical activity. More specifically, compounds of the present invention include nucleoside analogues having antineoplastic activity. These compounds seemingly function as antimetabolites with additional utility in Boron Neutron Capture Therapy (BNCT).

INTRODUCTION

Antimetabolites are a well known class of antineoplastic agents that function by interfering with nucleic acid sythesis and consequently, replication within the target cells. Some of these compounds structurally mimic biosynthetic precursors of the naturally occurring nucleic acids, which are essential for replication and cell survival. By replacing these precursors, but without exhibiting the same biological effect, these compounds disrupt replication resulting in the demise of the the target cell.

Many antimetabolites have significant antiviral and antitumor activity and are incorporated in a variety of therapeutic regimens. But despite the therapeutic benefits of such compounds, their use is often accompanied by deleterious side effects, e.g. nausea, alopecia, and bone marrow depression. Accordingly, a great deal of interest has focused on synthesizing new analogues with improved therapeutic indexes.

We have recently discovered that boron containing nucleotides may be one class of improved nucleic acid analogues. Some exemplary boronated nucleotides are described in copending, commonly owned U.S. patent application Ser. No. 443,781 of B. Spielvogel, A. Sood, I. Hall, and B. Ramsay-Shaw titled "Oligoribonucleoside and Oligodeoxyribonucleoside Boranophosphates" and filed Nov. 30, 1989, which is incorporated herein by reference. There we describe, for example, boronated oligonucleotides that contain a boron functionality attached to internucleotide phosphorus.

Boron containing compounds are also useful in an antineoplastic regimen known as Boron Neutron Capture Therapy (BNCT). Soloway, A. H., *Progress in Boron Chemistry*; Steinberg, H., McCloskey, A. L., Eds.; the Macmillan Company: New York, 1964; Vol. 1, Chapter 4, 203-234. BNCT requires two components (Boron-10 and low energy thermal neutrons) for a radiotoxic reaction. The inherent advantage is that each component can be manipulated independently to produce the desired radiation effect. Boron-10 has a high cross section for thermal neutrons and after neutron capture, the particles generated, Li & $\alpha$, are relatively large by radiation standards and thus have a relatively short track in tissue, 10–14 microns. The Boron-10 is non-radioactive and for use in BNCT, its compounds do not have to be cytotoxic towards tumor cells. Thermal neutrons have such low energy that they cannot ionize tissue components per se. Upon neutron capture, however, the energy generated is sufficient to destroy the cell. The problem in making this procedure clinically effective has stemmed not from the concept, per se, but from lack of knowledge in medicinal chemistry, nuclear engineering and physics, immunology, physiology and pharmacology. The present invention arose from our continued research on new boron-containing compounds having pharmaceutical activity.

SUMMARY OF THE INVENTION

A first aspect of the present invention is a boronated nucleoside comprising a nucleoside which is N-boronated on the nucleoside base with a boron-containing substituent selected from the group consisting of $-BH_2CN$, $-BH_3$, and $-BH_2COOR$, wherein R is C1 to C18 alkyl. Preferably, R is C1 to C9 alkyl, and most preferably R is C1 to C4 alkyl.

A second aspect of the present invention is a boronated nucleotide comprising a 5' phosphate ester of a boronated nucleoside as described above.

A third aspect of the present invention is a boronated oligonucleotide comprising a chain of natural or modified ribonucleotides or deoxyribonucleotides, at least one nucleotide of said oligonucleotide comprising a boronated nucleotide as described above.

Nucleosides of the present invention have pharmaceutical activity, including antihyperlipidemic, antiinflammatory, and antineoplastic activity. Nucleotides of the present invention are useful as intermediates for making oligonucleotides of the present invention. Oligonucleotides of the present invention are useful as antisense agents and probes.

A method for synthesizing N-boronated nucleosides of the present invention from a substrate nucleoside, which substrate nucleoside is comprised of a ribose moiety covalently bound to a nitrogenous base, is also disclosed. The method comprises:

(a) protecting the hydroxy substituents of the ribose; then (b) boronating the nitrogenous base; and then (c) deprotecting the hydroxy substituents. Preferably, the nitrogenous base is boronated by reacting the substrate nucleoside with either polymeric $BH_2CN$ or LX, wherein L is a Lewis base and X is a boron-containing substituent selected from the group consisting of $-BH_2CN$, $-BH_3$, and $-BH_2COOR$, wherein R is as given above.

The term alkyl, as used herein, refers to linear or branched alkyl groups which may be saturated or unsaturated. Preferred alkyl groups are linear and saturated.

DETAILED DESCRIPTION OF THE INVENTION

We have successfully synthesized novel boronated nucleosides that have surprising antineoplastic, antiinflammatory and antihyperlipidemic properties. The present invention provides novel pharmaceutical agents, methods for their synthesis, methods for treating patients in need of such treatment, and pharmaceutical formulations comprising such agents.

The nucleosides of the present invention comprise nucleosides having a boron-containing substituent on the base. More specifically, the present invention provides N-boronated nucleosides wherein the boronated nitrogen is a ring nitrogen of the base covalently bonded to the boron of the boron-containing substituent. The base is a purine or a pyrimidine or an analog thereof (as discussed in detail below). A preferred group of bases are those selected from the group consisting of adenine, cytosine, guanine, inosine, and the analogs thereof.

By nucleosides we mean a purine or pyrimidine base, and analogs thereof, linked to a pentose. The pentose is preferably D-ribose, 2'-deoxy-D-ribose or 2',3'-dideoxy-D-ribose. Thus the nucleosides of the present invention include both naturally occurring nucleosides and analogs thereof.

In the case of a purine nucleoside, boronation occurs preferentially at either the N1 or N7 position depending upon the purine. For example, when the purine is adenine, boronation occurs at the N1 position. In the case of guanine, boronation occurs at the N7 position. It is contemplated that boronation at other nitrogens on the nitrogenous bases will yield additional useful agents.

The nucleoside base may generally be a natural base, such as adenine, thymine, cytosine, guanine, uracil, xanthine, or hypoxanthine, (the latter two being the natural degradation products) or an analog thereof as found in, for example, 4-acetylcytidine; 5-(carboxyhydroxyl- methyl)uridine; 2'-O-methylcytidine; 5-carboxymethyl- aminomethyl-2-thiouridine; 5-carboxymethylaminomethyl-uridine; dihydrouridine; 2'-O-methylpseudo-uridine; beta,D-galactosylqueosine; 2'O-methylguanosine; N6-isopentenyladenosine; 1-methyladenosine; 1-methylpseudo-uridine; 1-methylguanosine; 1-methylinosine; 2,2-dimethylguanosine; 2-methyladenosine; 2-methylguanosine; 3-methyl-cytidine; 5-methylcytidine; N6-methyladenosine; 7-methylguanosine; 5-methylaminomethyluridine; 5-methoxyamino-methyl-2-thiouridine; beta,D-mannosylqueosine; 5-methoxy-carbonylmethyluridine; 5-methoxyuridine; 2-methylthio-N6-isopentenyladenosine; N-((9-beta-D-ribofuranosyl-2-methylthiopurine-6-yl)carbamoyl)threonine; N-((9-beta-D-ribofuranosyl-purine-6-yl)N-methyl-carbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'O-methyluridine. Preferred analogs are the methylated analogs.

Exemplary boronated nucleosides of the present invention are:
(A) guanosine-N7-cyanoborane;
(B) inosine-N7-cyanoborane;
(C) adenosine-N1-cyanoborane;
(D) cytidine-N3-cyanoborane;
(E) guanosine-N7-borane;
(F) inosine-N7-borane;
(G) adenosine-N1-borane;
(H) cytidine-N3-borane;
(I) guanosine-N7-carbomethoxyborane;
(J) inosine-N7-carboethoxyborane;
(K) adenosine-N1-carbopropoxyborane;
(L) cytidine-N3-carbobutoxyborane;
(M) 2'-deoxyguanosine-N7-cyanoborane;
(N) 2'-deoxyinosine-N7-cyanoborane;
(O) 2'-deoxyadenosine-N1-cyanoborane;
(P) 2'-deoxycytidine-N3-cyanoborane;
(Q) 2'-deoxyguanosine-N7-borane;
(R) 2'-deoxyinosine-N7-borane;
(S) 2'-deoxyadenosine-N1-borane;
(T) 2'-deoxycytidine-N3-borane;
(U) 2'-deoxyguanosine-N7-carbomethoxyborane;
(V) 2'-deoxyinosine-N7-carboethoxyborane;
(W) 2'-deoxyadenosine-N1-carbopropoxyborane;
(X) 2'-deoxycytidine-N3-carbobutoxyborane;
(Y) 2',3'-dideoxyguanosine-N7-cyanoborane;
(Z) 2',3'-dideoxyinosine-N7-cyanoborane;
(AA) 2',3'-dideoxyadenosine-N1-cyanoborane;
(AB) 2',3'-dideoxycytidine-N3-cyanoborane;
(AC) 2',3'-dideoxyguanosine-N7-borane;
(AD) 2',3'-dideoxyinosine-N7-borane;
(AE) 2',3'-dideoxyadenosine-N1-borane;
(AF) 2',3'-dideoxycytidine-N3-borane;
(AG) 2',3'-dideoxyguanosine-N7-carbomethoxyborane;
(AH) 2',3'-dideoxyinosine-N7-carboethoxyborane;
(AI) 2',3'-dideoxyadenosine-N1-carbopropoxyborane; and
(AJ) 2',3'-dideoxycytidine-N3-carbobutoxyborane.

Particularly preferred boronated nucleosides are: 2'-deoxyguanosine-N7-cyanoborane, 2'-deoxyinosine-N7-cyanoborane, 2'-deoxyadenosine-N1-cyanoborane, and 2'-deoxycytidine-N3-cyanoborane.

The nucleosides of the present invention further comprise 5,-phosphate esters of the N-boronated nucleosides described herein, such phosphate esters are also known as nucleotides. Such nucleotides, particularly the monophosphates, are protected in conventional manner and used for the synthesis of oligonucleotides, as discussed below. Such phosphate esters include 5' mono-, di- and triphosphates, which may be protected as esters. Additionally, molecules and macromolecules comprising multimers of two or more nucleosides, which may be linked via a 3'-5' phosphate ester, e.g. oligonucleotides (the terms "oligonucleotides" and "polynucleotides" being used interchangeably herein), and comprising one or more N-boronated nucleosides are also the subject of the present invention. Accordingly, N-boronated nucleotides, oligonucleotides, and polynucleotides may be used as therapeutic agents and otherwise useful reagents, e.g. diagnostic reagents.

Oligonucleotides of the present invention can be synthesized in accordance with methods that are well known in the art. Such methods include the phosphite method and the phosphotriester method. 1 Chemistry of Nucleosides and Nucleotides, 294ff (L. Townsend ed. 1988). The length of the oligonucleotide is not critical, as modern synthetic techniques and splicing techniques have made synthetic oligonucleotides of considerable length feasible. Thus, the oligonucleotide may for example be 2 to 3 nucleotides long, 2 to 18 nucleotides long, 2 to 30 nucleotides long, 2 to 50 nucleotides long, or 50 or more nucleotides long.

Oligonucleotides containing N-boronated bases may alternatively be prepared, with boronation occurring randomly, in essentially the same manner as the nucleoside, but with an oligonucleotide substituted for the nucleoside. For example, in such a reaction, the 3' terminus of the oligonucleotides may be immobilized to a solid support (e.g., controlled pore glass), the 5' terminus protected as the dimethyltrityl ether, and amino groups on bases protected with isobutyryl groups. Oligonucleotides used for such a reaction preferably contain at least one base which is not thymidine or a thymidine analog, as these are less preferred bases for boronation.

Derivatives of the oligonucleotides and polynucleotides may additionally be formed by modifying the internucleotide phosphodiester linkage. Internucleotide phosphodiester linkages in the chain are modified, for example, to the methylphosphonate, the phosphotriester, the phosphorothioate, the phosphorodithioate, and the phosphoramidate, all as is known in the art.

Additional synthetic analogues of the nucleosides, nucleotides, and oligonucleotides of the present invention may be formed by otherwise modifying the 3' or 5' end of the nucleoside, and any 2' hydroxyl groups.

Groups that can be added to the 3' or 5' end vary widely, from relatively inert protecting groups to reactive groups or groups with special properties to obtain desireable physical, chemical, or biochemical effects.

A wide variety of protecting groups can be substituted on the 2', 3', and 5' hydroxy groups, such as the triphenylmethyl (trityl) group and its derivatives on the 5' hydroxy group, and acetyl, benzoyl, or the 3'-O-succinyl group on the 3' hydroxy group, as is known in the art. See 1 Chemistry of Nucleosides and Nucleotides, 287-92 (L. Townsend ed. 1988). In general, the 5' hydroxy group is protected with an acid labile group and the 3' hydroxy group is protected with an acyl group. Id. at 289 (When the 5' hydroxyl group is protected with an acid labile group such as mono- and dimethoxytrityl, the 3'-hydroxyl group of deoxynucleosides can be protected with acyl groups.). In general, a 2' hydroxy group is protected as a methyl ether, protected with a silyl group, or the 2' and 3' hydroxy groups may be protected together as an acetal.

Reactive groups or groups with special properties may also be attached at the 3' or 5' position. For example, analogs may be formed by joining an intercalating agent to oligonucleotides and polynucleotides in the manner described in U.S. Pat. No. 4,835,263 to Nguyen et al. (the disclosure of this and all other patent references cited herein is incorporated herein by reference).

The present invention also provides methods for preparing the compounds of the present invention. The boronation of a nucleoside is accomplished by first preparing a hydroxy- protected nucleoside. Protecting groups and methods for their use are well known in the art. See, Carey and Sundberg, *Advanced Organic Chemistry*, Part B, pp. 408-414 (1980). Preferred protecting groups are organosilanes, e.g., chlorotriisopropyl silane will form the triisopropyl silyl ether.

As an example, the nucleoside is O-protected by forming a silyl ether by reaction with excess chlorotriisopropyl-silane at room temperature in the presence of imidazole. The exchange reaction is effected by reacting the O-protected nucleoside with an organoborane. The organoborane is generally either polymeric $BH_2CN$ or a compound LX, wherein L is a Lewis base and X is a boron-containing substituent as given above. Suitable Lewis bases include amine, phosphine, sulfide, and ether (e.g., tetrahydrofuran). The strength and steric properties of the Lewis base should be chosen so as to provide a suitable leaving group. Exemplary organoboranes include aniline-cyanoborane, triphenylphosphine-carboalkoxyboranes (wherein the alkoxy group alkyl is R as given above), dimethylsulfide-borane, and tetrahydrofuran-borane. A preferred organoborane is triphenylphosphine-cyanoborane, in which case the resulting product is an O-protected ribonucleoside N-cyanoborane. The exchange reaction is effected by reaction in anhydrous tetrahydrofuran (THF) at reflux temperature using two equivalents of triphenylphosphine-cyanoborane. The reaction is at equilibrium in two to three hours.

The resulting O-protected N-boronated ribonucleoside is deprotected by appropriate methods known in the art. For example, when protected by formation of a silyl ether, deprotection can be effected under hydrolytic or nucleophilic conditions. In our preferred case the silyl ether is effectively removed under hydrolytic conditions in the presence of fluoride ion, e.g., tetra-n-butylammonium fluoride.

The compounds of the present invention have pharmaceutical activity and are useful in treating mammals (e.g., human, cat, dog, cow, horse, mouse) suffering from one or more of several maladies. These compounds show pharmaceutical activity in killing cancer cells in vitro, and may be useful in combatting corresponding tumors in vivo. For example, the compounds of the present invention show cytotoxic activity against colorectal carcinoma, adenocarcinoma, osteosarcoma, breast carcinoma and glioma. Accordingly, the compounds of the present invention provide a method for treating a tumor bearing mammal comprising administering to said mammal a therapeutically effective amount of a boronated nucleoside of the present invention. Furthermore, it is contemplated that the antineoplastic efficacy of these compounds can be improved or supplemented by the conjoint administration with other known antineoplastic agents, as, for example, in a combination chemotherapy regimen. Exemplary of such other known antineoplastic agents are: vinca alkaloids such as vincristine, vinblastine, and vindesine; epipodophyllotoxins such as etoposide and teniposide; anthracycline antibiotics such as daunorubicin, doxorubicin, mitoxantraone, and bisanthrene; actinomycin D; and plicamycin.

In addition to the direct inhibition of tumor growth, the preferential localization of boron compounds in the neoplasm of tumor cells will allow the use of boron-10 neutron capture therapy (BNTC) for the destruction of tumor cells. Moreover, the dual effect of this therapeutic regimen may lower the therapeutically effective amounts of the pharmaceutically active agents, and thereby reduce the deleterious side effects that often accompany the use of such agents. Thus, the present invention also provides methods for treating tumor-bearing mammals in which the mammal is administered a boronated nucleoside as described herein and then exposed to thermal neutron radiation. The thermal neutron radiation is administered in an amount and in a manner effective for $^{10}B$ located in a tumor by virtue of the administration of the compound of the present invention to the subject to capture a neutron, decay, and release an alpha particle in cells of the tumor.

The compounds of the present invention also have pharmaceutical activity as antiinflammatory agents in mammals. The compounds of the present invention provide a method for treating a mammal suffering from inflammation comprising administering to said mammal a therapeutically effective amount of an N-boronated nucleoside. The compounds of the present invention may provide additional utility when conjointly administered with other known antiinflammatory agents or pain killers or some such pharmaceutical. Exemplary of other known antiinflammatory agents are acetylsalicylic acid (asprin), salicylic acid, diflunisal, phenylbutazone, oxyphenbutazone, antipyrine, aminopyrine, dipyrone, apazone, acetaminophen, indomethacin, sulindac, meclofenamate, tolmetin, zomepirac, ibuprofen, and piroxicam.

The compounds of the present invention are useful as hypolipidemic agents. The compounds of the present invention provide a method for treating a mammal suffering from hyperlipidemia comprising administering to said mammal a therapeutically effective amount of an N-boronated nucleoside. Additionally, the compounds of the present invention provide a method for treating a mammal suffering from hypercholesterolemia comprising administering to said mammal a therapeutically effective amount of an N-boronated nucleoside. By administering these compounds to hyperlipidemic patients the total lipoprotein level may be reduced or the lipoprotein profile may be improved. Furthermore, these compounds may be conjointly administered with other known hypolipedemic agents to enhance or supplement their efficacy. Exemplary of such other known hypolipidemic agents are nicotinic acid, clofibrate, gemfibrozil, probucol, cholestyramine, colestipol, compactin, mevinolin, choloxin, neomycin, and beta-sitosterol.

The compounds of the present invention may be administered in any of the variety of modes currently employed for analogous pharmaceutical agents, which modes are well known in the art. For example, these compounds may be administered systemically. Systemic administration includes parenteral administration and gastro-enteral administration.

When prepared in a pharmaceutical formulation for parenteral administration the compounds of the present invention should be prepared in a pharmaceutically acceptable carrier such as substantially non-pyrogenic, sterile, parenterally acceptable, aqueous solutions.

Alternatively, the compounds of the present invention may be formulated in pharmaceutical preparations for gastro-enteral administration. Such pharmaceutical preparations include tablets, capsules and suppositories. When formulated for administration according to any of the above methods the pharmaceutical preparations may further comprise buffers, binders, and other pharmaceutically acceptable excipients as are well known in the art.

A therapeutically effective amount of a boronated nucleoside is in the range of about 0.1-100 mg/kg/day. The preferred range is about 0.5-50 mg/kg/day. More preferred is an amount in the range of about 1-10 mg/kg/day. When administered conjointly with other pharmaceutically active agents even less of the boronated nucleoside may be therapeutically effective.

The oligonucleotides of the present invention may be used as probes in a variety of diagnostic techniques. One such diagnostic technique is Magnetic Resonance Imaging (MRI). MRI is a noninvasive technique used to detect the presence and location of tumors in a patient. For example, as contemplated in the present context, cancer cell specific boronated compounds are administered to a patient, whereupon they concentrate in cancerous tissue. The MRI instrument is capable of detecting and locating regions of abnormal concentrations of Boron. By indicating the regions having high relative concentrations of Boron, MRI establishes the presence and location of tumors.

Another diagnostic application of the oligonucleotides of the present invention is their use as molecular probes By incorporating N-boronated nucleosides, or their 5'-phosphate esters, into an oligonucleotide, either at an interior or terminal position, a detectable oligonucleotide probe is constructed that can be used to detect the presence of complementary sequences of DNA or RNA in a sample.

These probes can be used in any suitable environment, such as Southern blotting and Northern blotting, the details of which are known. See, e.g., R. Old and S. Primrose, Principles of Gene Manipulation, 8-10 (3d Ed. 1985). When used as probes, the boron atom serves as a radiolabel, though it is not itself radioactive until exposed to thermal neutron radiation (low energy neutrons). When exposed to low energy neutrons, $^{10}$B absorbs a neutron and forms $^{11}$B, which rapidly decays and releases an alpha particle, thus providing a detectable signal. The techniques involved in the generation of the alpha particle are known. See, e.g., A. Soloway, Borax Rev.3, 7-9 (1988).

Oligonucleotides of the present invention which are capable of binding to polyribonucleic acid or polydeoxyribonucleic acid are useful as antisense agents in the same manner as conventional antisense agents. See generally Antisense Molecular Biology and S-oligos, Synthesis 1 (Oct. 1988) (published by Synthecell Corp., Rockville, Md.); 2 Discoveries in Antisense Nucleic Acids (C. Brakel and R. Fraley eds. 1989). Antisense agents of the present invention may be used by contacting an antisense agent which is capable of selectively binding to a predetermined polydeoxyribonucleic acid sequence or polyribonucleic acid sequence to a cell containing such sequence (e.g., by adding the antisense agent to a culture medium containing the cell) so that the antisense agent is taken into the cell, binds to the predetermined sequence, and blocks transciption, translation, or replication thereof. The requirements for selective binding of the antisense agent are known (e.g., a length of 17 bases for selective binding within the human genome).

The present invention is explained in greater detail in the following non-limiting examples.

EXAMPLE I

A. Synthesis of 2'-Deoxyribonucleoside-N-Cyanoboranes

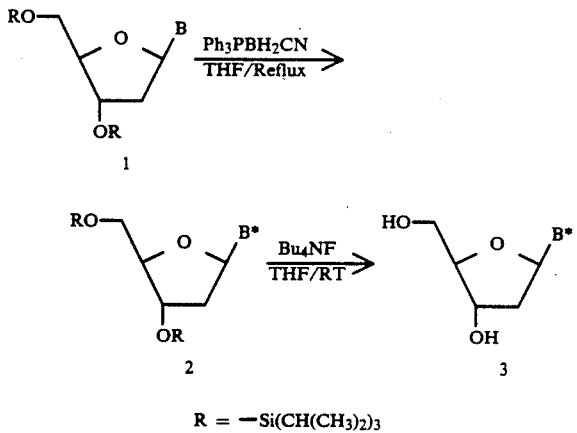

$R = -Si(CH(CH_3)_2)_3$

B = Gua (a), Ino (b), Ade (c), Cyt (d) or Thy (e)

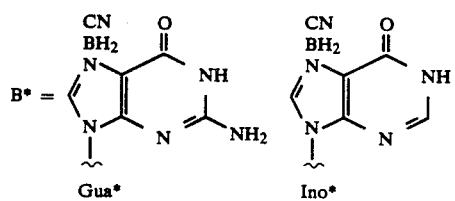

-continued
Scheme I

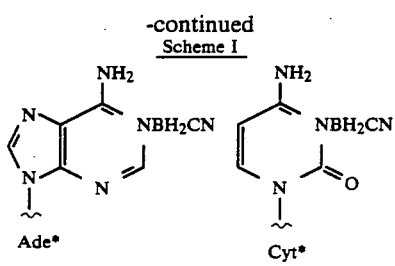

Cyanoborane adducts of 2'-deoxynucleosides, for example, 2'-deoxyguanosine-N7-cyanoborane (3a), 2'-deoxyinsoine-N7-cyanoborane (3b), 2'-dexoyadenosine-N1-cyanoborane (3c), and 2'-deoxycytidine-N3-cyanoborane (3d), were prepared by an exchange reaction of triphenylphosphine-cyanoborane (Ph$_3$PBH$_2$CN) with 3', 5'-O-protected nucleosides. The 3'- and 5'-Hydroxy groups were protected as silyl ethers by reaction with excess chlorotriisopropylsilane at room temperature in DMF in the presence of imidazole. The exchange was carried out in anhydrous THF at reflux temperature using 2 equiv of Ph$_3$PBH$_2$CN. No increase in the amount of product could be observed (by TLC) after 2-3 hours. The major products were purified by flash chromatography. Yields can be expected to be approximately 72% for the guanine derivative (2a), 59% for the adenine derivative (2c), 46% for the cytosine derivative (2d), and 26% for the hypoxanthine derivative (2b). While the first three adducts were readily purified, 2b was obtained only in ca. 95% purity (by $^1$HNMR). We have as yet been unsuccessful in preparing the boron-substituted thymidine derivative from 1e by exchange reaction with Ph$_3$PBH$_2$CN.

Deprotection of boronated nucleosides 2a–d with tetra-n-butylammonium fluoride (Bu$_4$NF) to give 3a–d was complete within 0.5 h. Purification was achieved by flash chromatography, followed by crystallization from MeOH/Et$_2$O. Satisfactory (within plus or minus 0.25%) C, H, N analyses were obtained for the final compounds. The yields ranged from 44% for 3d to 55% for 3b.

The site of boron coordination was determined by $^{15}$N NMR spectroscopy on a JEOL FX90Q instrument. No peak was observed for the cooordinated nitrogen (in both coupled and decoupled spectra) due to quadrupole broadening by boron. The absence of peaks for N7 of Gua* and Ino*, N1 of Ade*, and N3 of Cyt* established these to be the sites of BH$_2$CN coordination. When $^{15}$N NMR spectra of 2a and 2d were obtained on a GE GN500 system, the above quadrupole effect was not observed. In this case, upfield shifts of 56.6 ppm for N7 of Gua* and 50.1 ppm for N3 of Cyt* confirmed the assignments. The shifts upon boronation are qualitatively similar to but lower than those observed upon protonation (ca.65–70 ppm). The coordination site in Gua* and Ino* is away from the sites required for Watson-Crick base pairing and should not affect pairing to a large extent. Variable-temperature $^1$H NMR studies on the Gua*-Cyt base pair indeed show the H bonding to be approximately as strong as in a normal Gua-Cyt base pair. The coordination at N1 in Ade* and N3 in Cyt*, however, should completely disrupt the base pairing, and if incorporated into DNA, these nucleosides may lead to inhibition of replication.

By HPLC, compounds 3a, 3b, and 3d in aqueous medium (0.01 M TEAAc) are >94% stable over a period of 168 h. Compound 3b, however, is >50% decomposed during this period. The good stability of 3a, 3c, and 3d in aqueous medium makes these compounds suitable for pharmacological testing.

B. Experimental (1). 3',5'-O-Bis (triisopropylsilyl)-2'-deoxynucleosides

2'-Deoxynucleoside [In the case of 2'-deoxycytidine, the hydrochloride was used with an additional equivalent of imidazole] (19.90 mmol) and excess imidazole (96.36 mmol) were taken in anhydrous dimethylformamide (55 ml) under inert atmosphere. Chlorotriisopropylsilane (51.33 mmol) was added to this mixture and it was stirred at room temperature for 24 h. After dilution with diethylether (90 ml), it was washed with a saturated solution of sodium chloride (5×80 ml). The organic layer was filtered to remove any suspended solid, dried over anhydrous sodium sulfate and solvent was removed under reduced pressure to give crude product. Purification was achieved by flash chromatography on silica gel using a mixture of solvents (vide infra). The products were characterized by $^1$H nmr, $^{13}$C nmr, $^{15}$N nmr, infrared and FAB mass spectroscopic techniques.

(1a). 3', 5'-O-Bis(triisopropylsilyl)-2'-deoxyguanosine: Purification solvent: dichloromethane/acetone (6:4); yield=88.6%; Mp=decomp above 181° C.;

(1b). 3', 5'-O-Bis(triisopropylsilyl)-2'-deoxyinosine: Purification solvent: dichloromethane/acetone (6:4); Rf=0.33; yield=72.7%; Mp=158°–160° C. with prior shrinking between 63°–90° C.

(1c). 3', 5'-O-Bis(triisoproylsilyl)-2'-deoxyadenosine: Purification solvent: dichloromethane/acetone (8.5:1.5); Yield=46.8%; Mp=130.5°–131.5° C.

(1d). 3', 5'-O-Bis-(triisopropylsilyl)-2'-deoxycytidine: Purification solvent: dichloromethane/acetone (4:6); Rf=0.33; yield=83.7%; Mp=102° C. with prior shrinking and color change from white to transparent.

(2). 3', 5'-O-Bis(triisopropyl)-2'-deoxynucleosidecyanoborane adducts

3', 5'-O-Bis(triisopropylsilyl)-2'-dexoxynucleoside and triphenylphosphine-cyanoborane (2-fold) were taken in anhydrous THF under inert atmosphere and were heated at reflux. After ca 2-3 h, no further change in the ration of product to the starting material could be observed by tlc. The mixture was heated an additional hour, allowed to cool and the solvent was removed under reduced pressure. The residue was taken in diethyl ether, filtered and the solid was repeatedly washed with diethyl ether. The filtrate and the washings were concentrated and the crude product was purified by flash chromatography. The products were characterized by $^1$H nmr, $^{11}$B nmr, $^{13}$C nmr, $^{15}$N nmr, infrared and FAB mass spectroscopic techniques.

(2a). 3',5'-O-Bis(triisopropylsilyl)-2'-deoxyguanosine N7-cyanoborane: Purification solvent: dichloromethane/ acetone (8:2); yield=72.1%; Mp=170°–171° C.

(2b). 3', 5-O-Bis(triisopropylislyl)-2'-deoxyinosine-N7-cyanoborane: Purification solvent: dichloromethane/ acetone (7.5:2.5); Rf=0.43; yield=26.2%; contains ca 5% impurity.

(2c). 3', 5'-O-Bis(triisopropylsilyl)-2'-deoxyadenosine-N1-cyanoborane: Purification solvent: hexane/ethyl acetate (6:4); yield=58.6%; Mp=132.5–133.5, melts with decomposition.

(2d). 3′, 5′-O-Bis(triisopropylsilyl)-2′-deoxycytidine-N3-cyanoborane, 2d: Purification solvent: dichloromethane/acetone (9.25:0.75); Rf=0.40; yield=45.9%; Mp=164°–165° C.

3. 2′-Deoxynucleoside-cyanoborane adducts

To a solution of 3′, 5′-O-bis(triisopropylsilyl)-2′-deoxynucleoside-cyanoborane adduct (ca 1 g.) in tetrahydrofuran was added tetrabutylammonium fluoride (2 equivalent of 1.1M solution in tetrahydrofuran). The mixture was stirred at room temperature. After complete reaction (ca 0.5 h), the solvent was removed under reduced pressure. The residual oil was taken in diethyl ether (2×50 ml), stirred for a minute, allowed to stand for 5 minutes and then the ether was decanted. The residue was partially purified by flash chromatography on silica gel using dichloromethane/methanol (8.5:1.5). Fractions containing the desired product were concentrated and the still impure product was finally purified by crystallization from methanol/Et$_2$O. The products were characterized by $^1$H nmr, $^{11}$B nrm, $^{13}$C nmr, infrared and FAB mass spectroscopic techniques and elemental analysis. Yields of ~45% and better are obtained.

(3a). 2′-Deoxyguanosine-N7-cyanoborane: yield=45.5%; Mp=decomp. above 198° C.

(3b). 2′-Deoxyinosine-N$^7$-cyanoborane: yield=54.7%; Mp=decomp. above 173° C.

(3c). 2′-Deoxyadenosine-N1-cyanoborane: yield=47.3%; Mp=decomp. above 150° C.

(3d). 2′ Deoxycytidine-N3-cyanoborane: yield=44.3%; Mp=decomp. above 144° C.

EXAMPLE II

Cytotoxic Activity

In studies on the antitumor activity, these compounds, particularly 3c and 3d, showed potent activity in, among others, the T molt-3 and human colorectal adenocarcinoma screens. More specifically, the cytotoxic activity of the boron adducts of the present invention was tested on the following neoplastic cell lines:

1. L1210 lymphoid leukemia cells, R. Geran et al., *Cancer Chemotherapy Reports* 3, 7 (1972).(grown in RPMI+15% FBS+antibiotics).

2. Tmolt$^S$ acute lymphoblastic T cell leukemia, S. Schreiber and N. Ikemoto, *Tett. Lett* 29, 3211 (1988) (grown in RPMI - 1640+10% FBS).

3. Colon adenocarcinoma SW480 human colorectal carcinoma. A. Leibovitz et al., *Cancer Res.* 36, 4562 (1976) (grown in L15+10% FBS).

4. Lung bronchogenic MB-9812, S. Aronson et al., *Expt. Cell Res.* 61, 1 (1970) (grown in EMEM+10% FBS+NEAA).

5. Human Osteosarcoma TE418. H. Smith et al., *Int. J. Cancer* 17, 219 (1976) (grown in DMEM+10% FBS).

6. KB epidermoid oral nesopharnyx. R. Geran, supra: H. Eagle, *Proc. Soc. Expt. Biol.* 89, 362 (1955)(grown in EMEM +5% calf serum).

7. Hela-S, ATCC-CCL 2.2, cervical carcinoma suspended, S. Schreiber and N. Ikemoto, supra; T. Puck et al., *J. Exp. Med.* 103. 273 (1956) (grown in Joklik+5% FBS, Ham's F$_{12}$+5% FBS).

8. Breast carcinoma MDA MB157,W. Nelson-Rees et al., *Int. J. Cancer* 16, 74 (1975) (grown in EMEM+10% FBS +NEAA).

9. Human glioma cell EH 118 MG transformed stain of Rous sarcoma virus, J. Lutton et al., *J. Biol. Chem.* 254, 11181 (1979) (grown in DMEM-H+10% FCS).

The cytotoxic screens were conducted according to NIH protocols, see E. Huang et al., *J. Pharm. Sci.* 61, 108 (1972), with 10$^4$ cells, growth medium, antibiotics and drugs from 0.5 to 100 μg/ml final concentration. For the L1210, Hela-S, amd Tmolt, (i.e. the suspended cells), the incubations were conducted in sterile test tubes in a final volume of 1 ml for 72 hr at 37° C. in a CO$_2$ incubator. The cells on the third day were still in log growth phase. The number of cells/ml are determined using trypan blue exclusion and a hemocytometer. See, e.g., R. Geran, supra. For solid tumors there is plated out in wells 1×10$^4$ cells with 1 ml of medium-+antibiotics and the other components of growth. When the controls have converged (≈95%) then the density of the cells is estimated and the ED$_{50}$ values calculated. These structures are given in Table I below, and these data are given in Table II below.

TABLE I

| | Structure of Compounds | | | |
|---|---|---|---|---|
| | Deoxyribose | | Nucleoside Base | |
| | 3′ | 5′ | N$_1$ | N$_7$ |
| 3b Ino | OH | OH | H | BH$_2$CN |
| 2b Ino | Si(CH(CH$_3$)$_2$)$_3$ | Si(CH(CH$_3$)$_2$)$_3$ | H | BH$_2$CN |
| 3a Gua | OH | OH | H | BH$_2$CN |
| 2a Gua | Si(CH(CH$_3$)$_2$)$_3$ | Si(CH(CH$_3$)$_2$)$_3$ | H | BH$_2$CN |
| 3c Ade | OH | OH | BH$_2$CN | H |
| 2c Ade | Si(CH(CH$_3$)$_2$)$_3$ | Si(CH(CH$_3$)$_2$)$_3$ | BH$_2$CN | H N$_3$ |
| 3d Cyt | OH | OH | BH$_2$CN | — |
| 2d Cyt | Si(CH(CH$_3$)$_2$)$_3$ | Si(CH(CH$_3$)$_2$)$_3$ | BH$_2$CN | — |
| 4. Cyt | H | Si(CH(CH$_3$)$_2$)$_3$ | BH$_2$CN | — |

TABLE II

Cytotoxicity of Boron Adducts of ribonucleosides

| Cpd. | L1210 | P388 | Tmolt | Adeno Carcinoma SW480 | KB | Lung Bronchogenic | Hela-S | Osteo sarcoma | Glioma |
|---|---|---|---|---|---|---|---|---|---|
| 3b | 4.00 | 7.21 | 1.73 | 3.86 | 3.45 | 4.93 | 2.41 | 7.28 | 8.49 |
| 2b | 4.00 | 7.31 | 6.49 | 2.57 | 5.29 | 6.20 | 3.26 | NA | 6.21 |
| 3a | 5.08 | 5.87 | | | | | | | |
| 2a | 6.05 | 5.13 | 2.26 | 2.67 | 2.67 | 4.05 | 2.83 | 7.20 | 7.61 |
| 3c | 3.68 | 5.96 | 1.36 | 2.82 | 3.12 | 5.26 | 2.35 | 7.39 | 6.88 |
| 2c | 6.86 | 7.46 | 1.88 | 2.87 | 5.79 | 5.58 | 3.42 | NA | 4.99 |
| 3d | 2.61 | 3.17 | 1.13 | 2.96 | 5.46 | 3.73 | 3.37 | 4.63 | 4.39 |
| 2d | 4.78 | 7.26 | 3.36 | 2.73 | 5.72 | 6.60 | 2.94 | NA | 6.77 |
| 4. | 2.92 | — | 2.34 | 2.71 | 4.07 | 5.58 | 3.63 | 6.62 | 3.43 |

EXAMPLE III

Antihyperlipidemic Activity

Compounds to be tested were suspended in 1% aqueous carboxymethylcellulose, homogenized and administered to male $CF_1$ mice (25 g) intraperitoneally for 16d. On days 9 and 16, blood was obtained by tail vein bleeding, and the serum was separated by centrifugation for three minutes. The serum cholesterol levels were determined by a modification of the Liebermann—Burchard reaction in accordance with known techniques. See A. Ness, et al., *Clin. Chim. Acta* 10, 229 (1964). Serum triglyceride levels were determined with a commercial kit, the Fisher Hycel Triglyceride Test Kit, for a different group of animals bled on day 16. The results of these antihyperlipidemic screens, for a compound dose of 8 mg/kg, are shown in Table III below.

EXAMPLE IV

Anti-Inflammatory Activity $CF_1$ male mice (~25 g) were administered test drugs at 5-40 mg/kg in 0.05% Tween 80—$H_2O$ intraperitoneally 3 hours prior to and 30 minutes prior to the injection of 0.2 ml of 1% carrageenan in 0.9% saline into the plantar surface of the right hind foot. Saline was injected into the left hind foot, which serves as a base line. After 3 hours, both feet were excised at the tibiotarsal (ankle) joint according to standard procedures. See C. Winter et al., *Proc. Soc. Expt. Biol Med.* 544, 111 (1962); A. Roszkawski et al., *J. Pharm. Exp. Ther.* 179, 114 (1971). Control mice afforded a 78±3 mg increase in paw weight. Data on the percent inhibition of the inflammatory response for a dose of 8 mg/kg are reported in Table III below.

TABLE III

Antiinflammatory and Hypolipidemic Activities of Boron-Containing Nucleosides

| Compound | Antiinflammatory Activity at 8 mg/kg/day % inhibition | Hypolipidemic | |
|---|---|---|---|
| | | Cholesterol Inhibition at 8 mg/kg/day % inhibition | Triglyceride Inhibition at 8 mg/kg/day % inhibition |
| 3a | 22 | 44 | 37 |
| 3b | 25 | 19 | 30 |
| 3c | 22 | 44 | 37 |
| 3d | 52 | 38 | 23 |
| Standard | 47 (phenyl-butazone) | 13 (clofibrate at 130 mg/kg/day)n | 25 |

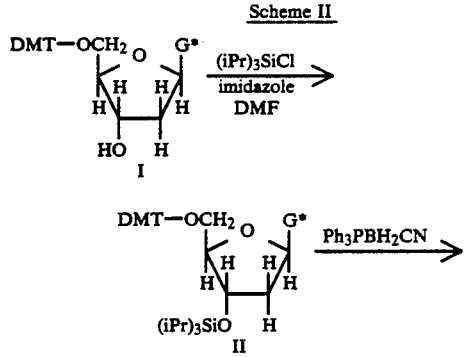

Scheme II

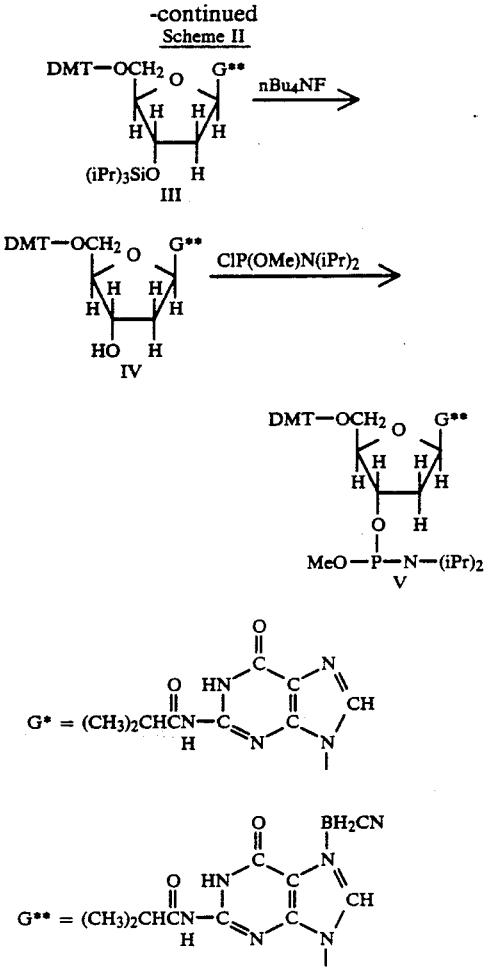

Step 1

Preparation of 5'-DMT-3'-TIPSI-$N^2$-isobutyryl-2'-deoxyguanosine

Starting nucleoside I (930 mg) and imidazole (1.188 g) were dissolved in 10 ml anhydrous DMF under Argon. To this was added chlorotriisopropylsilane (1.5 ml) and the mixture was stirred at room temperature. TLC ($CH_2Cl_2$/MeOH 9:1) after 1 hour indicated very little reaction. The mixture was allowed to stir for 22 hours. TLC of the reaction mixture ($CH_2Cl_2$:MeOH: [:9.5:0.5]) showed only a trace amount of starting material left. The mixture was stirred for another 2 hours, diluted with $Et_2O$ (30 ml) and washed with saturated NaCl(4×20 ml). The $Et_2O$ layer was dried and the solvent was removed in vacuo. The residue was purified by flash chromatography using $CH_2Cl_2$:MeOH (9.6:0.4). Yield=671 mg. II

Step 2

Preparation of 5'-DMT-3'-TIPSI-$N^2$-isobutyryl-2'-deoxyguanosine-$N^3$-cyanoborane A mixture of starting nucleoside II (0.455 g) and $Ph_3PBH_2CN$ (1:2 ratio respectively) in anhydrous THF (35 ml) under argon was heated at reflux for 3 hours. The reaction mixture was cooled in ice and then the solvent was removed in vacuo. The residue was purified by flash chromatography on silica gel using CH$_2$Cl$_2$:Acetone (9.5:0.5). Fractions 24–60 (=20 ml each) contained pure product and were combined. The solvent was removed under reduced pressure. Yield=0.163 g. III

Step 3

Preparation of 5'-DMT-N$^2$-isobutyryl-2'-deoxyguanosine-N$^7$-cyanoborane

Starting nucleoside III (0.163 g) was dissolved in THF. To this was added 1 equivalent of nBu$_4$NF (1.1M solution in THF) and the mixture was stirred at room temperature. After 40 min. the reaction was checked by TLC (CH$_2$Cl$_2$:MeOH [91:9]), which indicated that only a small amount of starting material had reacted to give the product. After 2½ hours, TLC showed an increase in amount of product, but starting material was th more intense spot. After 4½ hours, TLC was similar to that after 2½ hours so another 180 μl of nBu$_4$NF was added and the mixture was stirred at r.t. for 40 min. TLC of the reaction mixture indicated almost complete reaction. The solvent was removed from the reaction mixture under reduced pressure. The residue was purified by flash chromatography on silica using CH$_2$Cl$_2$:MeOH (9.4:0.6). Yield=110 mg. IV.

Step 4

Preparation of N$^2$-isobutyryl-5'-DMT-N$^7$-cyanoborane-2'-deoxyguanosine-3'(methyldiisopropyl) phosphoramidite Starting nucleoside IV (110 mg) in a three neck r.b. flask was evacuated and then flushed with argon. Diisopropyl ethyl amine (iPr$_2$NEt) followed by CH$_2$Cl$_2$ were added. After complete dissolution of nucleoside, diisopropylmethyl phosphonamidic chloride (47 μl) was added dropwise. The mixture was stirred at r.t. After 25 min. a few drops of reaction mixture were taken in a mixture of EtOAc/water. TLC of the EtOAc solution was was developed in EtOAc:CH$_2$Cl$_2$:Et$_3$N (4.5:4.5:1). Only a trace amount of reaction had occurred so another 1 equiv. of phosphonoamidic chloride was added and the mixture was allowed to stir. After 2½ hours, only a trace amount of reaction had occurred. After 4½ hours, another equivalent of amidic chloride was added. After 7 hours, =0.1 ml of MeOH was added and the solution was diluted with EtOAc: 7–8 ml. It was washed with =10% NaHCO$_3$ (2×5 ml) and sat. NaCl (2×5 ml). The organic layer was dried and solvent was removed under reduced pressure. Purification was attempted by flash chromatography using CH$_2$Cl$_2$:MeOH (97:3). The major spots eluted with other impurities. The product was recolumned using CH$_2$Cl$_2$:EtOAc (8:2). It still did not come out as a single or even two spots (for two diastereomers), instead 3–4 more polar spots (although in small amounts) were present. The $^{31}$P nmr shows less than 5% impurities and 1H nmr of this material shows no impurity other than solvents used for column. The product was further dried in vacuo. Yield 11.0 mg V.

The foregoing examples are illustrative of the present invention, and are not to be taken as limiting thereof. The invention is defined by the following claims, with equivalents of the claims to be included therein.

That which is claimed is:

1. A boronated nucleoside comprising a nucleoside which is N-boronated on the nucleoside base with a boron-containing substituent selected from the group consisting of —BH$_2$CN, —BH$_3$, and —BH$_2$COOR, wherein R is C1 to C18 alkyl.

2. A boronated nucleotide comprising a 5' phosphate ester of a nucleoside according to claim 1.

3. A boronated oligonucleotide comprising a chain of ribonucleotides or deoxyribonucleotides, at least one nucleotide or said oligonucleotide comprising a nucleotide according to claim 2.

4. A boronated nucleoside according to claim 1 wherein the boron-containing substituent is —BH$_2$CN.

5. A boronated nucleoside according to claim 1 wherein the base of said nucleoside is selected from the group consisting of adenine, cytosine, guanine, and inosine.

6. A boronated nucleoside according to claim 1 selected from the group consisting of:
guanosine-N7-cyanoborane;
inosine-N7-cyanoborane;
adenosine-N1-cyanoborane;
cytidine-N3-cyanoborane;
guanosine-N7-borane;
inosine-N7-borane;
adenosine-N1-borane;
cytidine-N3-borane;
guanosine-N7-carbomethoxyborane;
inosine-N7-carboethoxyborane;
adenosine-N1-carbopropoxyborane;
cytidine-N3-carbobutoxyborane;
2'-deoxyguanosine-N7-cyanoborane;
2'-deoxyinosine-N7-cyanoborane;
2'-deoxyadenosine-N1-cyanoborane;
2'-deoxycytidine-N3-cyanoborane;
2'-deoxyguanosine-N7-borane;
2'-deoxyinosine-N7-borane;
2'-deoxyadenosine-N1-borane;
2'-deoxycytidine-N3-borane;
2'-deoxyguanosine-N7-carbomethoxyborane;
2'-deoxyinosine-N7-carboethoxyborane;
2'-deoxyadenosine-N1-carbopropoxyborane;
2'-deoxycytidine-N3-carbobutoxyborane;
2',3'-dideoxyguanosine-N7-cyanoborane;
2',3'-dideoxyinosine-N7-cyanoborane;
2',3'-dideoxyadenosine-N1-cyanoborane;
2',3'-dideoxycytidine-N3-cyanoborane;
2',3'-dideoxyguanosine-N7-borane;
2',3'-dideoxyinosine-N7-borane;
2',3'-dideoxyadenosine-N1-borane;
2',3'-dideoxycytidine-N3-borane;
2',3'-dideoxyguanosine-N7-carbomethoxyborane;
2',3'-dideoxyinosine-N7-carboethoxyborane;
2',3'-dideoxyadenosine-N1-carbopropoxyborane;
2',3'-dideoxycytidine-N3-carbobutoxyborane.

7. A boronated nucleoside selected from the group consisting of 2'-deoxyguanosine-N7-cyanoborane, 2'-deoxyinosine-N7-cyanoborane, 2'-deoxyadenosine-N1-cyanoborane, 2'-deoxycytidine-N3-cyanoborane, and 2',3'-dideoxycytidine-N3-cyanoborane.

8. A pharmaceutical formulation comprising an effective anti-inflammatory or anti-tumor amount of a boronated nucleoside in a pharmaceutically acceptable carrier, said boronated nucleoside comprising a nucleoside which is N-boronated on the nucleoside base with a boron-containing substituent selected from the group consisting of —BH$_2$CN, —BH$_3$, and —BH$_2$COOR, wherein R is C1 to C18 alkyl.

9. A pharmaceutical formulation according to claim 8 wherein the boronated nucleoside is selected from one or more of the group consisting of 2'-deoxyinosine-N7-cyanoborane, 2'-deoxyadenosine-N7-cyanoborane, 2'-deoxycytidine-N1-cyanoborane, and 2'-deoxycytidine-N3-cyanoborane.

10. A boronated oligonucleotide comprising a chain of 2 to 50 ribonucleotides or deoxyribonucleotides, at least one nucleotide of said oligonucleotide comprising a nucleotide according to claim 2.

11. A boronated oligonucleotide comprising a chain of 2 to 30 ribonucleotides or deoxyribonucleotides, at least one nucleotide of said oligonucleotide comprising a nucleotide according to claim 2.

12. A boronated oligonucleotide comprising a chain of 2 to 18 ribonucleotides or deoxyribonucleotides, at least one nucleotide of said oligonucleotide comprising a nucleotide according to claim 2.

13. A method for treating a mammal suffering from inflammation comprising administering to said mammal an effective anti-inflammatory amount of a boronated nucleoside comprising a nucleoside which is N-boronated on the nucleoside base with a boron-containing substituent selected from the group consisting of $-BH_2CN$, $-BH_3$, and $-BH_2COOR$, wherein R is C1 to C18 alkyl.

14. A method according to claim 13, wherein the boronated nucleoside is selected from the group conssiting of 2'-deoxyguanosine-N7-cyanoborane, 2'-deoxyinosine-N7-cyanoborane, 2'-deoxyadenosine-N1-cyanoborane, and 2-'-deoxycytidine-N3-cyanoborane.

* * * * *

UNITED STATES PATENT AND TRADEMARK OFFICE
CERTIFICATE OF CORRECTION

PATENT NO. : 5,130,302
DATED : 14 July 1992
INVENTOR(S) : Bernard F. Spielvogel, Anup Sood, Iris H. Hall, and Barbara Ramsay Shaw It is certified that error appears in the above-identified patent and that said Letters Patent is hereby corrected as shown below:

Column 4, line 16, please change "5," to --5'--.

Column 17, line 1, please change "deoxyinosine" to --deoxyguanosin--.

Column 17, line 2, please change "deoxyadenosine" to --deoxyinosine--.

Column 17, line 3, please change "deoxycytidine" to --deoxyadenosine--.

Signed and Sealed this

Twelfth Day of October, 1993

Attest:

BRUCE LEHMAN

*Attesting Officer*  *Commissioner of Patents and Trademarks*